United States Patent [19]

Konno et al.

[11] 4,406,688
[45] Sep. 27, 1983

[54] HERBICIDAL 4-BENZOYL-5-PHENACYLOXY-PYRAZOLE DERIVATIVES, COMPOSITION AND METHOD

[75] Inventors: Kazuhiko Konno; Atsushi Goh; Kazuhito Miyoshi; Kaoru Ikeda, all of Ami, Japan

[73] Assignee: Mitsubishi Petrochemical Co., Ltd., Japan

[21] Appl. No.: 313,970

[22] Filed: Oct. 22, 1981

[30] Foreign Application Priority Data

Oct. 27, 1980 [JP] Japan .................. 55-149308

[51] Int. Cl.³ .................. A01N 43/56; C07D 231/20
[52] U.S. Cl. .................. 71/92; 548/377; 548/367
[58] Field of Search .................. 548/377; 71/92

[56] References Cited

U.S. PATENT DOCUMENTS 4,146,726  3/1979  Konotsune et al. .................. 548/377
4,230,481  10/1980  Nishiyama et al. .................. 548/377
4,266,963  5/1981  Nishiyama et al. .................. 548/377

FOREIGN PATENT DOCUMENTS 55-33454  3/1980  Japan.

Primary Examiner—Henry K. Jiles
Assistant Examiner—Natalia Harkaway
Attorney, Agent, or Firm—Wenderoth, Lind & Ponack

[57] ABSTRACT

A herbicidal compound having the following formula

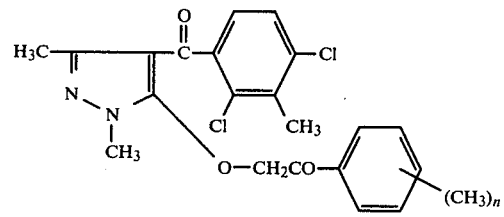

wherein n is 0 or 1; a herbicidal composition comprising said compound as an active ingredient; a process for producing said composition; and a herbicidal method employing said compound.

12 Claims, 1 Drawing Figure

Fig. 1

HERBICIDAL 4-BENZOYL-5-PHENACYLOXY-PYRAZOLE DERIVATIVES, COMPOSITION AND METHOD

This invention relates to a herbicidal compound which is not specifically described in the prior literature, a herbicidal composition comprising said compound as an active ingredient, a process for producing said composition, and a method for controlling weeds.

More specifically, this invention pertains to a pyrazole-type herbicidal compound which with low phytotoxicity, exhibiting excellent herbicidal activity at lower dosages than known analogous herbicidal compounds of the pyrazole-type and is more than about 10 times as safe as the known analogous herbicidal compounds of the pyrazole type in regard to fish toxicity which is of importance in rice paddy weed control; a composition comprising said compound as an active ingredient; a process for producing said composition; and a method for controlling weeds by using said herbicidal composition.

The herbicidal compound provided by this invention is a new compound of the following formula wherein n is 0 or 1.

According to the weed controlling method of the invention, there can be provided crops protected from weeds by the herbicidal compound of formula (1).

Several pyrazole-type herbicidally active compounds have been known heretofore. It is known that some of these compounds are characterized in that they cause chlorosis in weeds and also wither them and exhibit strong herbicidal activity on perennial weeds which are difficult to control by other herbicides. These pyrazole-type herbicides are disclosed, for example, in Japanese Laid-Open Patent Publications Nos. 126830/1975 (corresponding to U.S. Pat. Nos. 4,063,925 and 4,146,726), 41872/1979 (corresponding to U.S. Pat. No 4,230,481), 80269/1979, and 33454/1980.

The present inventors have found that these pyrazole herbicides have technical problems to be solved. For example, to obtain a satisfactory herbicidal effect, they should be used in relatively large amounts, and at low dosages, their herbicidal effect on noxious weeds such as toothcup, American waterwort, spikerush, bulrush and *Cyperus serotinus* is inferior. Furthermore, since they have to be applied in relatively large amounts, they may cause fish toxicity in paddy weed control. Thus, the present inventors have made extensive investigations in order to solve these technical problems.

These investigations have led to the discovery that 4-(2,4-dichloro-3-methylbenzoyl)-1,3-dimethyl-5-phenacyloxypyrazole compounds of the following general fomula wherein n is 0 or 1, which may be encompassed within the general formula (A) described in the above-cited Japanese Laid-Open Patent Publication No. 33454/1980 but are not specifically disclosed in this Japanese patent document can be produced easily in good yields.

It has also been found that the compounds of formula (1) is an unexpected and unique herbicidally active compound which can give a solution to all of the aforesaid technical problems.

The Japanese Laid-Open Patent Publication No. 33454/1980 mentioned only trichloro compounds by name as compounds having three substituents on the phenyl nucleus of the benzoyl group at the 4-position. It does not even give physical and chemical data and herbicidal data of these trichloro compounds. It is stated in this Japanese patent document that compounds of formula (A) having an especially good herbicidal effect are those in which n is 1 or 2, and among these compounds, those in which $X_n$ is 2,4-dichloro or 2-chloro-4-nitro are especially superior. However, this patent document totally fails to suggest or disclose compounds of formula (A) in which the 4-position is substituted by 2,4-dichloro-3-methyl-benzoyl and their unique herbicidal activity. Moreover, this patent document does not even refer to fish toxicity.

Investigations of the present inventors have led to the discovery that among three most analogous compound in which the 4-position is substituted by monomethyl-substituted-2,4-dichlorobenzoyl, only those compounds of formula (1) in accordance with this invention in which the 4-position is substituted by 3-methyl-2,4-dichlorobenzoyl have a broad herbicidal spectrum against noxious weeds which have been unable to be controlled at low dosages, such as barnyard grass, *Monochoria vaginalis*, toothcup, American waterwort, spikerush, bulrush, *Cyperus serotinus*, and *Sagittaria pygmaea*, as shown by comparative tests given hereinbelow. It has also been unexpectedly found that the fish toxicity of these compounds is more than about 10 times as low as that of 4-(2,4-dichlorobenzoyl)-1,3-dimethyl-5-phenacyloxypyrazole, a typical conventional compound of the pyrazole-type, and the compounds of the invention do not substantially cause toxicity to rice plants and other agricultural crops.

It is an object of this invention therefore to provide a pyrazole-type herbicidal composition comprising the compound of formula (1) as an active ingredient and exhibiting unique herbicidal properties.

Another object of this invention is to provide a process for producing the aforesaid herbicidal composition, and a method for controlling weeds by using the compound of formula (1).

The above and other objects and advantages of this invention will become apparent from the following description.

The herbicidal compound of formula (1) of this invention can be produced in high yields by an easy operation by reacting a new compound of the following formula with a compound of the following formula wherein Hal represents a halogen atom, and n is 0 or 1, in the presence of a basic acid binder.

The compound of formula (2) used in the production of the compound of formula (1) can be easily produced in good yields by reacting 1,3-dimethyl-5-pyrazolone of formula (4) with a 2,4-dichloro-3-methylbenzoyl halide of formula (5) in the presence of an acid binder, as schematically shown below.

In formula (5), Hal is preferably Cl or Br. The above reaction is preferably carried out in a solvent, for example ethers or mixtures thereof such as tetrahydrofuran, dioxane or tetrahydrofurandioxane; halogenated hydrocarbons such as dichloromethane and carbon tetrachloride.; and secondary or tertiary alcohols such as isopropanol and tert-butanol. The ethers and tertiary alcohols are especially preferred.

The acid binder used in this reaction is, for example, an alkali metal carbonate or alkaline earth metal hydroxide, such as potassium carbonate, sodium carbonate and calcium hydroxide. Potassium carbonate is especially preferred. The amount of the acid binder can be preferably selected as desired, and is, for example, about 1 to about 2 moles per mole of the 1,3-dimethyl-5-pyrazolone (4). The reaction temperature can also be selected as desired, and is, for example, room temperature to the refluxing temperature of the solvent. The reaction is preferably carried out at the refluxing temperature of the solvent or a temperature close to it. The reaction time can be selected as desired. For example, it is about 1 to about 20 hours. The resulting compound of formula (2) can be separated from the reaction mixture in a customary manner, for example by diluting the reaction mixture with water, acidifying it, and extracting it with an organic solvent. If desired, the product can further be subjected to a purifying means such as column chromatography and recrystallization.

The 2,4-dichloro-3-methylbenzoyl halide of formula (5) used in the above reaction can be easily prepared by acetylating 2,6-dichlorotoluene of formula (6) [for example, by the method described in Chem. Abs. 42, 1228b (1948)], treating the resulting 2',4'-dichloro-3'-methylacetophenone derivative of formula (7) with an oxidizing agent such as nitric acid or chromic acid, and treating the resulting 2,4-dichloro-3-methylbenzoic acid of formula (8) with a halogenating agent such as thionyl chloride, phosphorus pentachloride and phosphorus tribromide, as schematically shown below.

The treatment with the oxidizing agent can be performed, for example, by the following procedure. Preferably, it is carried out by using an excess of nitric acid. For example, about 2 to about 10 moles of nitric acid may be used per mole of the compound of formula (7). The reaction can be performed in the presence or absence of a solvent such as a lower fatty acid (e.g., acetic acid or propionic acid). The concentration of the nitric acid used may, for example, be 10 to 40%. The reaction temperature may, for example, be 60° to 150° C., and the reaction time is 1 to 12 hours although it varies with the reaction temperature. After the reaction, the reaction mixture is poured into a large excess of cold water, and the precipitated solid is filtered or extracted to form the final product in crude form. It may be purified further by recrystallization or other conventional means.

The halogenation treatment after the treatment with the oxidizing agent is performed preferably by using an excess of a thionyl halide. For example, about 2 to about 5 moles of the thionyl halide is used per mole of 2,4-dichloro-3-methylbenzoic acid. The reaction can be carried out at the refluxing temperature for about 1 to about 5 hours. After the reaction, the excess of the thionyl halide is distilled off under reduced pressure to give a crude product. The crude product may be purified by such a method as distillation under reduced pressure.

The herbicidal compound (1) can be prepared by reacting the compound of formula (2) with the compound of formula (3) in the presence of a basic acid binder, as stated above. The reaction is carried out, preferably in the presence of a solvent, at a temperature ranging from room temperature to the refluxing temperature of the solvent, preferably at the refluxing temperature or a temperature close to it, for a period of, say, about 1 to about 30 hours.

The reaction is carried out in the presence of a basic acid binder. In a modified embodiment, the compound of formula (2) is first contacted with the basic acid binder to form a salt of the compound of formula (2), and the salt is then reacted with the compound of formula (3).

Examples of the basic acid binder used in this reaction include inorganic bases such as sodium carbonate, potassium carbonate and sodium hydrogen carbonate; and organic based such as pyridine and triethylamine.

Examples of the solvent used are ethers such as diethyl ether, tetrahydrofuran and dioxane, aromatic hydrocarbons such as benzene, toluene and xylene, halogenated hydrocarbons such as dichloromethane, chloroform and carbon tetrachloride, ketones such as acetone and methyl ethyl ketone, esters such as ethyl acetate, acetonitrile, dimethyl formamide, dimethyl sulfoxide, and mixtures of these.

The amount of the compound of formula (3) used in the reaction may be selected as desired. For example, it is about 1 to about 1.5 moles per mole of the compound of formula (2). The amount of the basic acid binder is, for example, about 1 to about 2 moles per mole of the compound of formula (2). After the reaction, the solvent is distilled off, and as required, the residue is acidified with hydrochloric acid and extracted with chloroform. The extract is washed with water and dried, and chloroform is distilled off to recover the compound of formula (1). The compound may be purified by recrystallization from a solvent such as toluene.

Examples of the compound of formula (1) are 4-(2,4-dichloro-3-methylbenzoyl)-1,3-dimethyl-5-phenacyloxypyrazole, and 4-(2,4-dichloro-3-methylbenzoyl)-1,3-dimethyl-5-(o-, m- or p-methylphenacyl)oxypyrazole represented by the following formulae.

-continued

The herbicidal compound (1) of this invention produced in the above manner is useful for producing the herbicidal composition of this invention by mixing it with a known agriculturally acceptable carrier or diluent.

Thus, according to this invention, there is also provided a herbicidal composition composed of a herbididally effective amount of a compound of the formula (1)

wherein n is 0 or 1, and a carrier or diluent.

The carrier or diluent may be a solid or liquid carrier or diluent, and if desired, the composition may further contain other agriculturally acceptable adjuvants. Examples of the carrier or diluent include inorganic solid materials such as talc, clay, kaolin, montmorillonite, diatomaceous earth and calcium carbonate; organic solid materials such as organic plant materials (e.g., starth, wheat, wood fluor, and crystalline cellulose), natural or synthetic polymer compounds (e.g., polyalkylene glycols, ketone resin, ester gum, or copal gum), or urea, and liquid materials such as water, alcohols, benzene, xylene, toluene, methylnaphthalene, dimethyl sulfoxide, carbon tetrachloride, chloroform, trichloroethylene, dioxane, tetrahydrofuran, and nonionic, anionic, cationic and amphoteric surface-active agents (preferably the nonionic and anionic surfactants).

The liquid carriers or diluents which can be used in this invention are not limited to solvents for the herbicidal compound of formula (1), but may include nonsolvents therefor which can serve to disperse or dissolve the compound of the invention in the presence of adjuvants.

Examples of the adjuvants include spreaders such as polyoxyethylene aryl ethers, polyoxyethylene alkylphenyl ethers, alkylaryl polyglycol ethers and sodium dinaphthylmethanesulfonate; emulsifiers such as polyoxyethylene lauryl ether, polyoxyethylene alkylphenyl ethers, polyoxyethylene palmitate, polyoxyethylene sorbitan monolaurate, sorbitan monolaurates, and polyethylene glycol laurates; wetting agents such as alkylpolyether alcohols, polyoxyethylene alkylphenyl ethers, polyethylene glycol oleate, sodium alkylaryl polyethersulfonate and sodium isopropylaphthalenesulfonate; and dispersants such as alkylphenyl polyethoxyethanols, sodium alkylnaphthalenesulfonates, sodium alkylbenzenesulfonates, sodium alkylarylsulfonates and polyoxyethylene nonyl phenyl ether.

Inclusion of such adjuvants can ensure the herbicidal efficacy of the herbicidal composition of this invention.

The herbicidal composition of this invention may be in various forms, such as wettable powders, dusts, emulsifiable concentrates, granules, particles, aerosols, The herbicidal compound of formula (1) of this invention can also be used together with aother herbicide, a plant growth regulator, a fungicide, or a fertilizer, or as a composition containing such additional ingredients. Examples of such other herbicidally active compounds are S-(4-chlorobenzyl)-N,N-diethylthiolcarbamate (to be referred to as Benthiocarb), S-ethyl-N,N-hexamethylenethiolcarbamate (to be referred to as Molinate), 2-chloro-2',6'-diethyl-N-(butoxymethyl)acetanilide (to be referred to as Butachlor), 2-chloro-2',6'-diethyl-N-(N-propoxyethyl) acetanilide (to be referred to as CG-113), and S-(α,α-dimethylbenzyl) 1-piperidinecarbothioate (to be referred to as MY-93).

The ratio of the herbicidal compound (1) of the invention to the other herbicidally active compound may be selected as desired depending upon the types and combinations of the herbicidal components used, the kind of weeds to be controlled, the stage of weed growth, the time of application, the climatic conditions, etc. For example, the weight ratio of the compound of formula (1) to the other herbicidal compound is from 1:about 0.05 to 1:about 5.

By using the herbicidal compound of this invention, unwanted weeds in the cultivation of useful crops can be subjected to pre-emergence and post-emergence treatments to kill the weeds, inhibit their growth, prevent their emergence, etc.

Accordingly, the invention can also provide a method for controlling weeds which comprises applying a herbicidally effective amount of a compound of the formula wherein n is 0 or 1, to the locus where weeds are growing or will grow.

The herbicidal compound (1) may be applied singly, or in the form of the aforesaid composition. The amount of the active compound of formula (1) in the composition is, for example, about 1 to about 70% by weight based on the weight of the composition. The rate of application is, for example, about 10 to about 2000 g/10 ares, preferably about 50 to about 500 g/10 ares, as the active ingredient. The dosage may be changed properly depending upon the place of application, the weather, the kind of the weeds, etc.

The herbicidal compound (1) of this invention exhibits an excellent control effect against aquatic paddy weeds, for example annual weeds including broadleaf weeds such as toothcup (*Rotala indica*), *Monochoria vaginalis*, American waterwort (*Elatine triandra*), false pimpernel (*Lindernia pyxidaria*) and *Dopatrium junceum*, gramineous weeds such as barnyard grass (*Echinochloa crus-galli*), weeds of the family Cyperus such as *Cyperus difformis;* and perennial weeds including broadleaf weeds such as *Sagittaria pygmaea* and narrowleaf waterplantain (*Alisma canaliculatum*), and weeds of the family Cyperus such as *Cyperus serotinus*, spikerush (*Eleocharis acicularis*) and bulrush (*Scirpus juncoides*). It has low phytotoxicity, low toxicity and low fish toxicity.

The herbicidal compound (1) is applied preferably before emergence and/or in the early stage of growth of weeds.

The compound (1) of the invention can also be utilized for the control of weeds in upland farms. Examples of the upland farm weeds to be controlled include crabgrass (*Digitaria adscendens*), goosegrass (*Eleusine indica*), red root pig weed (*Amaranthus retroflexus*), lamb's quaters (*Chenopodium album Linnaeus*), goosefoot (*Chenopodium album* Linnaeus var. *centrorubrum* Makino), velvet leaf (*Abutilon theophrasti*), prickly sida (*Sida spinosa*) Beggarsticks (*Bidens pilosa*), common rag weed (*Ambrosia artemisiifolia*), common purslane (*Portulaca oleracea*), hairy galinsoga (*Galinsoga ciliata*), and dayflower (*Commelina communis*).

The following examples illustrate the present invention more specifically. All parts therein are by weight.

EXAMPLE 1

Synthesis of a herbicidal compound:

2,4-Dichloro-3-methylbenzoyl chloride

A 500 ml. three-necked flat-bottomed flask equipped with a reflux condenser, a thermometer and a Teflon agitator inside was charged with 205 g (1.0 mole) of 2,4-dichloro-3-methylbenzoic acid and 300 g (2.5 moles) of thionyl chloride. With stirring, they were reacted at 80° C. for 2 hours. The reaction mixture was cooled to room temperature, and the excess of thionyl chloride was distilled off by a rotary evaporator. The residue was dried under reduced pressure to give crude 2,4-dichloro-3-methylbenzoyl chloride as yellow crystals containing a small amount of a yellowish brown liquid. This product was distilled under reduced pressure to recover a fraction having a boiling point of 125° to 128° C. at 6 mmHg which was the desired product having a high purity. The amount of 2,4-dichloro-3-methylbenzoyl chloride obtained was 176.2 g (yield 79 mole%). The product had a melting point of 43.2° to 47.2° C. The structure of the 2,4-dichloro-3-methylbenzoyl chloride was determined by infrared absorption spectroscopy, mass spectroscopy, NMR spectroscopy and elemental analysis.

4-(2,4-Dichloro-3-methylbenzoyl)-1,3-dimethyl-5-hydroxypyrazole 11.2 g (0.1 mole) of 1,3-dimethyl-5-pyrazolone and 9.6 g (0.13 mole) of calcium hydroxide were suspended in 165 ml of isopropanol, and with stirring, the suspension was heated under reflux for 30 minutes. The reaction mixture was cooled, and 22.4 g (0.1 mole) of 2,4-dichloro-3-methyl-benzoyl chloride was added dropwise. After the addition, the mixture was heated under reflux for 10 hours. The solvent was distilled off from the reaction mixture, and 40 ml of water was added. The mixture was acidified with 65 ml of 2 N hydrochloric acid, and extracted with 100 ml of chloroform twice. The extracts were washed with water, and dried over magnesium sulfate. The solvent was distilled off, and the residue was recrystallized from toluene to give 14.9 g of colorless crystals (yield 49.8%; melting point 148.9°–149.5° C.).

4-(2,4-Dichloro-3-methylbenzoyl)-1,3-dimethyl-5-phenacyloxypyrazole (compound No. 1)

27.0 g (0.09 mole) of 4-(2,4-dichloro-3-methylbenzoyl)-1,3-dimethyl-5-hydroxypyrazole obtained as above and 24.8 g (0.18 mole) of potassium carbonate were suspended in 150 ml of methyl ethyl ketone, and with stirring, 17.9 g (0.09 mole) of phenacyl bromide was added. The mixture was heated under reflux for 7 hours. The solid was filtered, and washed with chloroform. The filtrate and the washing were combined, and the solvent was distilled off. The residue was washed with 30 ml of cooled methyl ethyl ketone to give 26.2 g of colorless crystals (yield 69.9%; melting point 149.5° to 151.5° C.).

EXAMPLE 2

Synthesis of a herbicidal compound:

4-(2,4-Dichloro-3-methylbenzoyl)-1,3-dimethyl-5-(p-methylphenacyloxy)pyrazole (compound No. 2)

21 g (0.07 mole) of 4-(2,4-dichloro-3-methylbenzoyl)-1,3-dimethyl-5-hydroxypyrazole obtained in the same way as in Example 1 and 14.5 g (0.105 mole) of potassium carbonate were suspended in 200 ml of methyl ethyl ketone, and with stirring, the suspension was heated under reflux for 1 hour. The reaction mixture was cooled, and a solution of 14.9 g (0.07 mole) of p-methylphenacyl bromide in 100 ml of methyl ethyl ketone was added. The mixture was heated under reflux for 3 hours. The solid was filtered and washed with methyl ethyl ketone. The filtrate and the washing were combined, and the solvent was distilled off. Hexane (100 ml) was added to the remaining crude product, and with stirring under heat, about 5 ml of 1,2-dichloroethane was added. The resulting solution was cooled with ice water to separate it into two layers. On further cooling with stirring, the lower layer crystallized in about 10 minutes. The crystals were collected by filtration, and washed with 50 ml of hexane to give 21 g (0.049 mole) of the captioned compound as light brown crystals. Yield 70%. Melting point 96°–101° C. (at temperatures above the melting point, the product recrystallized and at 132° C., it was again melted).

IR (cm$^{-1}$): 1695, 1630.

EXAMPLE 3

Synthesis of a herbicidal compound:

1-(2,4-Dichloro-3-methylbenzoyl)-1,3-dimethyl-5-(p-methylphenacyloxy)pyrazole (compound No. 3)

21 g (0.07 mole) of 4-(2,4-dichloro-3-methylbenzoyl)-1,3-dimethyl-5-hydroxypyrazole prepared as in Example 1 and 14.5 g (0.103 mole) of potassium carbonate were suspended in 200 ml of acetonitrile. With stirring, the mixture was heated under reflux for 1 hour. The reaction mixture was cooled, and a solution of 14.9 g (0.07 mole) of p-methylphenacyl bromide in 100 ml of acetonitrile was added, and the mixture was heated under reflux for 1 hour. The solid product was filtered and washed with acetonitrile. The filtrate and the washing were combined, and the solvent was distilled off. The remaining crude product was recrystallized from a mixture of 10 ml of methyl ethyl ketone and 10 ml of n-heptane to give 19.6 g of crystals. Yield 65%. Melting point 132.4°–132.8° C.

IR (cm$^{-1}$): 1699, 1622.

EXAMPLE 4

Synthesis of a herbicidal compound:

4-(2,4-Dichloro-3-methylbenzoyl)-1,3-dimethyl-5-(m-methylphenacyloxy)pyrazole (compound No. 4)

Example 3 was repeated except that m-methylphenacyl bromide was used instead of p-methylphenacyl bromide. There was obtained 19.0 (yield 60%) of 4-(2,4-dichloro-3-methylbenzoyl)-1,3-dimethyl-5-(m-methylphenacyloxy)pyrazole. Melting point 152.7°–153.2° C.

EXAMPLE 5

Synthesis of a herbicidal compound:

4-(2,4-Dichloro-3-methylbenzoyl)-1,3-dimethyl-5-(o-methylphenacyloxy)pyrazole (compound No. 5)

Example 3 was repeated except that o-methylphenacyl bromide was used instead of p-methylphenacyl bromide. There was obtained 20.2 g (yield 67%) of 4-(2,4-dichloro-3-methylbenzoyl)-1,3-dimethyl-5-(o-methylphenacyloxy)pyrazole. Melting point 153.5°–154.1° C.

EXAMPLE 6

Formulation example:

Five parts of compound No. 1, 2, 3, 4, or 5 and 95 parts of a mixture of talc and clay were mixed and pulverized to form a dust. The dust may be directly sprayed in application.

EXAMPLE 7

Formulation example:

Twenty parts of compound No. 1, 2, 3, 4 or 5 of the invention, 75 parts of a 2:1 mixture of Zeeklite and clay, 3 parts of sodium alkylbenzenesulfonate and 2 parts of sodium dinaphthylmethanesulfonate were mixed and pulverized to form a wettable powder. In application, the wettable powder may be diluted with water.

EXAMPLE 8

Formulation example:

Twenty parts of the compound No. 1, 2, 3, 4 or 5 of the invention, 75 parts of xylene, and 5 parts of Sorpol (registered trademark) as an emulsifier were mixed to form an emulsifiable concentrate. In application, the emulsifiable concentrate may be diluted with water.

EXAMPLE 9

Formulation example:

Ten parts of the compound No. 1, 2, 3, 4 or 5 of the invention, 55 parts of bentonite, 30 parts of talc, 2 parts of sodium dodecylbenzenesulfonate and 3 parts of sodium ligninsulfonate were mixed and pulverized and granulated by a granulator to form granules in a customary manner.

EXAMPLE 10

Formulation example:

Seventy parts of the compound No. 1, 2, 3, 4 or 5 of the invention, 25 parts of Zeeklite and 5 parts of sodium ligninsulfonate were mixed and pulverized to form a wettable powder. In application, the wettable powder may be diluted with water.

Herbicidal Text Example 1

Paddy soil was put in each of pots having an inside diameter of 18 cm, and mixed with water with stirring to create a watered and soil-broken condition. Then, seeds of barnyard grass, bulrush toothcup, *Monochoria vaginalis* and American waterwort were sown in predetermined amounts in each of the pots. Two tubers of *Cyperus serotinus* and *Sagittaria pygmaea* and two yearling roots of spikerush were transplanted in each pot. A group of two young seedlings in the 2-leaf stage was transplanted in a depth of 1 cm. On the next day, water was gently poured into each pot to 3 cm above the soil. The pots were then left to stand in a greenhouse.

Three days later, a predetermined amount of each of the active compounds shown in Table 1 as a wettable powder diluted with water was poured into each pot by means of a pipette. Then, the plants were grown for 30 days in a glass greenhouse. The results of the test are shown in Table 1.

The herbicidal effect was evaluated in terms of the ratio of surviving weeds on a scale of 0 to 5 as follows. The phytotoxicity to the transplanted rice plants was rated on a scale of − to +++ as follows.

| Herbicidal effect | Ratio of surviving weeds |
|---|---|
| 5 | 0 |
| 4 | not more than 20% |
| 3 | above 20% but not more than 40% |
| 2 | above 40% but not more than 60% |
| 1 | above 60% but not more than 80% |

-continued

| Herbicidal effect | Ratio of surviving weeds |
|---|---|
| 0 | above 80% |

Phytotoxicity

The phytotoxicity ratio of a non-treated area is taken as 0%, and phytotoxicity is evaluated as follows:
- − No phytotoxicity (0%)
- ± Slight phytotoxicity (more than 0% but not more than 10%)
- + Low phytotoxicity (above 10% but not more than 30%)
- ++ Medium phytotoxicity (above 30% but not more than 50%)
- +++ Severe phytotoxicity (more than 50%)

The comparative compounds A, B, C and D in the table are as follows:

Comparative compound A

Comparative compound B

Comparative compound C

Comparative compound D

TABLE 1

| Active compounds tested | Dosage (g/10 ares) | Barnyard grass | Monochoria vaginalis | Tooth-cup | American water-wort | Spike-rush | Bulrush | Sagittaria pygmaea | Cyperus serotinus | Trans-planted rice |
|---|---|---|---|---|---|---|---|---|---|---|
| No. 1 | 200 | 5 | 5 | 5 | 5 | 5 | 5 | 5 | 5 | — |
|  | 100 | 5 | 5 | 5 | 5 | 4.5 | 5 | 5 | 5 | — |
|  | 50 | 5 | 5 | 5 | 5 | 4.5 | 4.5 | 5 | 4.5 | — |
| No. 2 | 200 | 5 | 5 | 5 | 5 | 5 | 5 | 5 | 5 | — |
|  | 100 | 5 | 5 | 5 | 5 | 5 | 5 | 5 | 5 | — |
|  | 50 | 5 | 5 | 5 | 5 | 4.5 | 4.5 | 5 | 4.5 | — |
| No. 3 | 200 | 5 | 5 | 5 | 5 | 5 | 5 | 5 | 5 | — |
|  | 100 | 5 | 5 | 5 | 5 | 5 | 5 | 5 | 5 | — |
|  | 50 | 5 | 5 | 5 | 5 | 4.5 | 4.5 | 5 | 4.5 | — |
| No. 4 | 200 | 5 | 5 | 5 | 5 | 5 | 5 | 5 | 5 | — |
|  | 100 | 5 | 5 | 5 | 5 | 4.5 | 5 | 5 | 4.5 | — |
|  | 50 | 4.5 | 5 | 5 | 5 | 4.5 | 4.5 | 5 | 4.5 | — |
| No. 5 | 200 | 5 | 5 | 5 | 5 | 5 | 5 | 5 | 5 | — |
|  | 100 | 5 | 5 | 5 | 5 | 4.5 | 4.5 | 5 | 4.5 | — |
|  | 50 | 4.5 | 5 | 5 | 5 | 4 | 4 | 4.5 | 4 | — |
| Comparative compound A | 200 | 0 | 1.5 | 1 | 1.5 | 1 | 1 | 1 | 2 | — |
|  | 100 | 0 | 0 | 0 | 0 | 0 | 0 | 0 | 1.5 | — |
|  | 50 | 0 | 0 | 0 | 0 | 0 | 0 | 0 | 1 | — |
| Comparative compound B | 200 | 1.5 | 3 | 2.5 | 2.5 | 1.5 | 1 | 2 | 2.5 | — |
|  | 100 | 1 | 2.5 | 1 | 2 | 1 | 0 | 1.5 | 1.5 | — |
|  | 50 | 0 | 2 | 0 | 1 | 0 | 0 | 1 | 0 | — |
| Comparative compound C | 200 | 5 | 5 | 3.5 | 3.5 | 4 | 4 | 5 | 4.5 | — |
|  | 100 | 4.5 | 4.5 | 3 | 2.5 | 3.5 | 3.5 | 4 | 4 | — |
|  | 50 | 4 | 4 | 2.5 | 2 | 3 | 3 | 4 | 3 | — |
| Comparative compound D | 200 | 4.5 | 5 | 3 | 3 | 4 | 4 | 4.5 | 4.5 | — |
|  | 100 | 4 | 4 | 2.5 | 2.5 | 3 | 3 | 4 | 3 | — |
|  | 50 | 3 | 2 | 2 | 2 | 2 | 1.5 | 2 | 2 | — |

Herbicidal Test Example 2

Upland farm soil was put in pots each having an inside diameter of 18 cm. Twenty seeds of wheat were sown in the pots, and soil containing seeds of crabgrass, redroot pigweed, velvet leaf and beggarticks was put in the pots to cover the wheat seeds 1.5 to 2 cm deep. A wettable powder of each of the active compound was diluted with water, and a predetermined amount of it was applied to the soil in the pots by means of a microsprayer. The pots were allowed to stand in a greenhouse. The plants were grown while the pots were occasionally watered. Thirty days after the treatment with the chemicals, the herbicidal effect and the degree of phytotoxicity were evaluated in the same way as in Test Example 1. The results are shown in Table 2.

TABLE 2

| Active compounds tested | Dosage (g/10 ares) | Crab-grass | Red root pigweed | Velvet leaf | Beggar-ticks | Wheat |
|---|---|---|---|---|---|---|
| No. 1 | 1000 | 3 | 5 | 4 | 2 | — |
|  | 500 | 2 | 4 | 2 | 1 | — |
|  | 250 | 1 | 3 | 1 | 0 | — |
|  | 125 | 0 | 2 | 0 | 0 | — |
| No. 3 | 1000 | 3 | 5 | 5 | 2 | — |
|  | 500 | 2 | 5 | 5 | 1 | — |
|  | 250 | 1 | 4.5 | 5 | 0 | — |
|  | 125 | 0 | 3.5 | 4.5 | 0 | — |
| C | 1000 | 1 | 1.5 | 0 | 0 | — |
|  | 500 | 0 | 1 | 0 | 0 | — |
|  | 250 | 0 | 0 | 0 | 0 | — |
|  | 125 | 0 | 0 | 0 | 0 | — |
| D | 1000 | 1 | 1 | 0 | 0 | — |
|  | 500 | 0 | 0 | 0 | 0 | — |
|  | 250 | 0 | 0 | 0 | 0 | — |
|  | 125 | 0 | 0 | 0 | 0 | — |

Herbicidal Test Example 3

In order to determine the relationship between the herbicidal activity of a test compound and its dosage, Herbicidal Test Example 1 was repeated except that Sagittaria pygmaea, Monochoria vaginalis and false pimpernel were used as test plants and Compound No. 1 and Comparative compound C were used as test chemicals.

The results are shown in Table 3.

TABLE 3

| Active compound | Dosage (g/10 ares) | Ratio of surviving weeds (%) | | |
|---|---|---|---|---|
|  |  | Monochoria vaginalis | Sagittaria pygmaea | False pimpernel |
| Compound No. 1 | 200 | 0 | 0 | 0 |
|  | 100 | 0 | 0 | 0 |
|  | 50 | 0 | 0 | 0 |
|  | 25 | 0 | 20 | 0 |
| Comparative Compound C | 200 | 0 | 0 | 0 |
|  | 100 | 7 | 7 | 7 |
|  | 50 | 20 | 25 | 25 |
|  | 25 | 75 | 85 | 65 |

Herbicidal Test Example 4

Paddy soil was put in concrete pots (50 cm×50 cm) outdoors, and mixed with water with stirring to create a soil-broken and watered state. Then, seeds of barnyard grass, bulrush, toothcup, Amercian waterwort and Monochoria vaginalis were sown in predetermined amounts in each pot. Furthermore, three tubers of Cyperus serotinus and 6 tubers of Sagittaria pygmaea were transplanted. Two yound seedlings in the 2-leaf stage were combined as a group, and four such groups were transplanted to a depth of 1 cm. On the next day, water was gently poured onto the pots to 3 cm above the soil. Four days later (when the weeds emerged), a 10% granular composition of each active compound prepared as in Example 9 was applied to the pot. Thirty days after the application, the ratio of surviving weeds was determined, and evaluated as in Test Example 1. The results are shown in Table 4.

TABLE 4

Ratio of surviving weeds (%)

TABLE 5

| Active compound | Dosage (g/10 ares) | Herbicidal effect | | | | | | | | | Phytotoxicity to rice |
|---|---|---|---|---|---|---|---|---|---|---|---|
| | | Barnyard grass | Monochoria vaginalis | Toothcup | Umbrella plant | Bulrush | Spikerush | Narrowleaf waterplantain | Sagittaria pygmaea | Cyperus serotinus | |
| Compound No. 1 | 40 + 10 | 5 | 5 | 5 | 5 | 5 | 5 | 5 | 5 | 5 | — |
| + Butachlor | 20 + 5 | 5 | 5 | 5 | 5 | 5 | 5 | 5 | 5 | 5 | — |
| Compound No. 3 | 40 + 5 | 4.5–5 | 5 | 5 | 5 | 5 | 5 | 5 | 5 | 5 | — |
| + Butachlor | 20 + 5 | 4.5 | 5 | 5 | 5 | 4.5 | 5 | 5 | 5 | 4.5 | — |
| Compound No. 1 | 40 + 10 | 5 | 5 | 5 | 5 | 5 | 5 | 5 | 5 | 5 | — |
| + CG-113 | 20 + 5 | 5 | 5 | 5 | 5 | 5 | 5 | 5 | 5 | 5 | — |
| Compound No. 3 | 40 + 10 | 4.5–5 | 5 | 5 | 5 | 5 | 5 | 5 | 5 | 5 | — |
| + CG-113 | 20 + 5 | 4.5 | 5 | 5 | 5 | 4.5 | 5 | 5 | 5 | 4.5 | — |
| Compound No. 1 | 50 + 50 | 5 | 5 | 5 | 5 | 5 | 5 | 5 | 5 | 5 | — |
| + Benthiocarb | 25 + 25 | 5 | 5 | 5 | 5 | 5 | 5 | 5 | 5 | 5 | — |
| Compound No. 3 | 50 + 50 | 5 | 5 | 5 | 5 | 5 | 5 | 5 | 5 | 5 | — |
| + Benthiocarb | 25 + 25 | 4.5 | 5 | 5 | 5 | 4.5 | 4.5 | 5 | 5 | 4.5–5 | — |
| Compound No. 1 | 50 + 50 | 5 | 5 | 5 | 5 | 5 | 5 | 5 | 5 | 5 | — |
| + Molinate | 25 + 25 | 5 | 5 | 5 | 5 | 5 | 5 | 5 | 5 | 5 | — |
| Compound No. 3 | 50 + 50 | 5 | 5 | 5 | 5 | 5 | 5 | 5 | 5 | 5 | — |
| + Molinate | 25 + 25 | 5 | 5 | 5 | 5 | 5 | 5 | 5 | 5 | 4.5 | — |
| Compound No. 1 | 50 + 50 | 5 | 5 | 5 | 5 | 5 | 5 | 5 | 5 | 5 | — |
| + MY-93 | 25 + 25 | 5 | 5 | 5 | 5 | 4.5 | 4 | 5 | 5 | 4.5 | — |

| Active compound | Dosage (kg/10 ares) | Monochoria vaginalis | Toothcup | American waterwort | Sagittaria pygmaea | Transplanted rice |
|---|---|---|---|---|---|---|
| No. 1 | 2 | 0 | 0 | 0 | 0 | — |
|  | 1 | 0 | 0 | 0 | 0 | — |
|  | 0.5 | 0 | 0 | 0 | 0 | — |
| No. 3 | 2 | 0 | 0 | 0 | 0 | — |
|  | 1 | 0 | 0 | 0 | 0 | — |
|  | 0.5 | 0 | 0 | 0 | 0 | — |
| C | 2 | 3 | 5 | 8 | 10 | — |
|  | 1 | 10 | 22 | 25 | 23 | — |
|  | 0.5 | 21 | 43 | 45 | 38 | — |

Herbicidal Test Example 5

Paddy soil was filled in concrete pots having a size of 50 cm × 50 cm × 50 cm, and water was added to simulate an aquatic rice paddy. Seeds of barnyard grass, *Monochoria vaginalis*, toothcup, umbrella plant (*Cyperus difformis*), bulrush and narrowleaf waterplantain were sown in predetermined amounts in the pot. Tubers of *Sagittaria pygmaea* and *Cyperus serotinus* and yearling buds of spikerush were transplanted. Furthermore, two rice seedlings in the 2-leaf stage were combined into one group, and four groups of rice seedlings were transplanted into the pots. Thereafter, the pots were each left to stand outdoors, and the plants were grown under natural conditions. Each of the mixed chemicals consisting of the herbicidal compound of the invention and a known herbicidal compound was formulated into a wettable powder and diluted with water. It was applied in a predetermined amount to the pots three days after sowing (when barnyard grass emerged). The herbicidal effects and phytotoxicities of the chemicals were determined thirty days after the application of the chemicals in the same way as in Test Example 1.

The results are shown in Table 5.

Fish Toxicity Test Example

A wettable powder of the compound No. 1 of the invention was prepared in accordance with Example 7, and diluted with water to a concentration of 5, 10, 20, 40, and 80 ppm, respectively. 1.5 Liters of each of the dilutions was put in each of 2-liter beakers. Five red killifish (body length 3 cm) were released into each of the beakers. The beakers were then placed in a constant temperature chamber at 20° C., and 96 hours later, the leathality of the red killifish was determined.

The above test procedure was repeated except that the comparative compound C was used instead of the compound No. 1.

Figure 1:
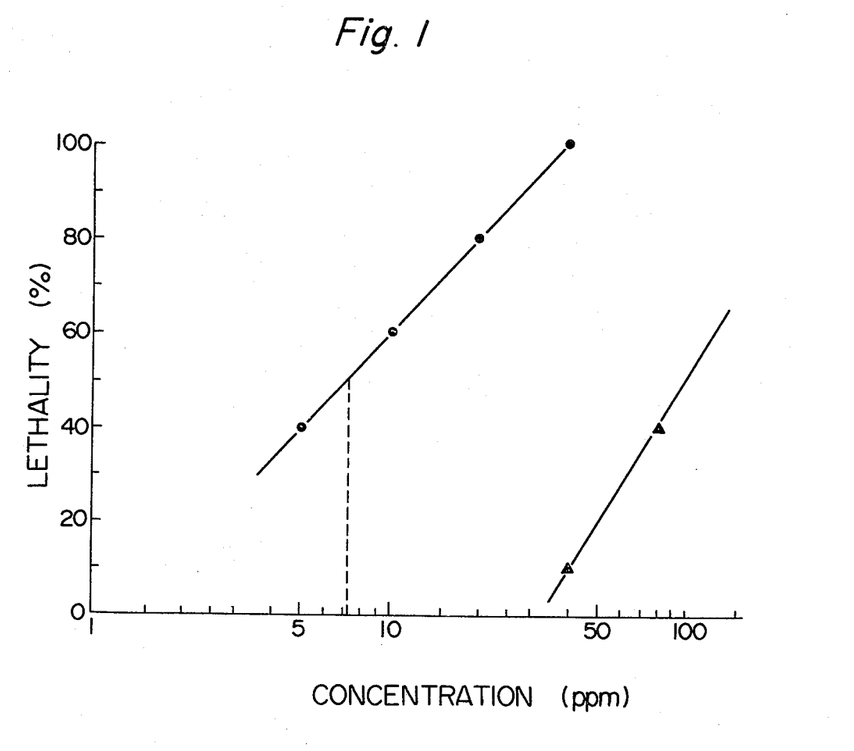

The results are plotted in FIG. 1 of the accompanying drawing in which the line with circular dots indicates the results obtained with the known compound C, and the line with triangular dots, the results obtained with the compound No. 1 of the invention.

FIG. 1 shows that $LD_{50}$ of the compound C is 7.2 ppm which is ranked in fish toxicity grade B according to "Standards of Safe Use Relating to Prevention of Damage to Aquatic Animals" in the Agricultural Chemicals Control Law of Japan whereas $LD_{50}$ of the compound No. 1 of the invention is more than 80 ppm which is ranked in Grade A showing low fish toxicity.

What is claimed is:

1. A compound having the following formula wherein n is 0 or 1.

2. The compound 4-(2,4-dichloro-3-methylbenzoyl)-1,3-dimethyl-5-phenacyloxy-pyrazole.

3. The compound 4-(2,4-dichloro-3-methylbenzoyl)-1,3-dimethyl-5-(p-methylphenacyloxy)pyrazole.

4. The compond according to claim 3 in the form of metastable crystals having a melting point of about 96°–101° C.

5. The compound according to claim 3 in the form of crystals having a melting point of about 132.4° to 132.8° C.

6. The compound 4-(2,4-dichloro-3-methylbenzoyl)-1,3-dimethyl-5-(m-methylphenacyloxy)pyrazole.

7. The compound 4-(2,4-dichloro-3-methylbenzoyl)-1,3-dimethyl-5-(o-methylphenacyloxy)pyrazole.

8. A herbicidal composition composed of a herbicidally effective amount of a compound of the following formula wherein n is 0 or 1, and a carrier or diluent.

9. The composition of claim 8 wherein the amount of the compound of formula (1) is about 1 to about 70% by weight based on the weight of the composition.

10. The composition of claim 8 wherein n is formula (1) is 1.

11. A method for controlling weeds which comprises applying a herbicidally effective amount of a compound of the following formula wherein n is 0 or 1, to the locus where weeds are growing or will grow.

12. The method of claim 11 wherein the rate of the compound of formula (1) applied is about 10 to about 2000 g/10 ares.

* * * * *